United States Patent
Usui et al.

(10) Patent No.: US 6,399,659 B2
(45) Date of Patent: Jun. 4, 2002

(54) HYDRAZINE OXOACETAMIDE DERIVATIVE AND INSECTICIDE

(75) Inventors: Syuichi Usui; Kiyoshi Takasuka; Yukinori Takekita; Junko Uchida; Norio Osaki, all of Tokorozawa (JP)

(73) Assignee: Agro-Kanesho Co., Ltd., Tokyo (JP)

( * ) Notice: Subject to any disclaimer, the term of this patent is extended or adjusted under 35 U.S.C. 154(b) by 0 days.

(21) Appl. No.: 09/837,656

(22) Filed: Apr. 19, 2001

Related U.S. Application Data

(63) Continuation of application No. PCT/JP99/05760, filed on Oct. 19, 1998.

(30) Foreign Application Priority Data

Oct. 19, 1998 (JP) .............................. 10-297240

(51) Int. Cl.[7] ..................... C07C 309/65; A61K 31/185
(52) U.S. Cl. ................... 514/517; 514/614; 558/47; 564/151
(58) Field of Search ................. 564/151; 514/517, 514/614; 558/47

(56) References Cited

U.S. PATENT DOCUMENTS 4,344,893 A * 8/1982 Copping .................... 548/557

FOREIGN PATENT DOCUMENTS

| DE | 19831803 | 4/1999 |
| JP | 8-41013 | 2/1996 |
| JP | 9-278744 | 10/1997 |

* cited by examiner

Primary Examiner—Robert Gerstl
(74) Attorney, Agent, or Firm—Oblon, Spivak, McClelland, Maier & Neustadt, P.C.

(57) ABSTRACT

The present invention relates to a hydrazine oxoacetamide derivative or its salt which exhibits an excellent insecticidal effect even at a low concentration. The hydrazine oxoacetamide derivative has the following Formula (I):

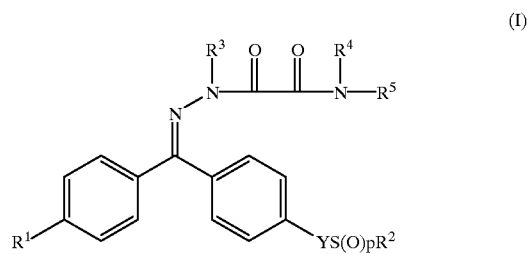

wherein $R^1$ represents a chlorine atom or a bromine atom, Y represents an oxygen atom or a methylene group, and when Y is an oxygen atom, p is 2 and when Y is a methylene group, p is 0, $R^2$ represents a trifluoromethyl group, $R^3$ represents a hydrogen atom or a methyl group, $R^4$ represents a hydrogen atom or a methyl group, and $R^5$ represents a methyl group, an ethyl group, an n-propyl group, a cyclopropyl group, an allyl group or a propargyl group.

10 Claims, No Drawings

HYDRAZINE OXOACETAMIDE DERIVATIVE AND INSECTICIDE

This application is a continuation of PCT/JP99/05760 filed Oct. 19, 1998.

BACKGROUND OF THE INVENTION

1. Field of the Invention

The present invention relates to a hydrazine oxoacetamide derivative or a salt thereof and a process for producing it, as well as use thereof as a pesticide, particularly, an insecticide.

2. Description of the Background

Several compounds have been known which are connected with a hydrazine oxoacetamide derivative and which have an insecticidal activity. Examples of these compounds include the compounds having the following Formulae (II) to (IV) disclosed in

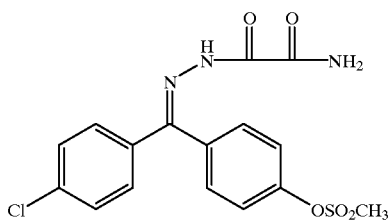
(II)

the specification of U.S. Pat. No. 4,394,387:
(shown as Compound No. 255)
(shown as Compound No. 230), and

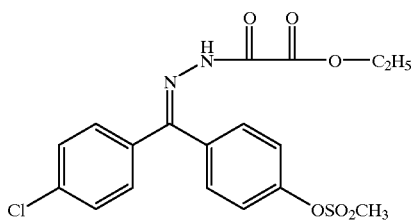
(IV)

(shown as Compound No. 257).

A compound having the following Formula (V) is described in Japanese Patent (J.P.) Kokai No. Hei 10-67732:

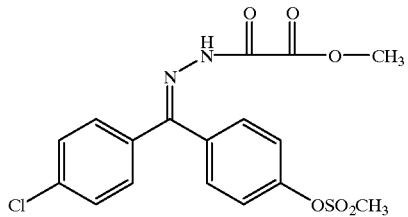
(V)

A compound having the following Formula (VI) is described in International Publication (WO) No. 97/11050:

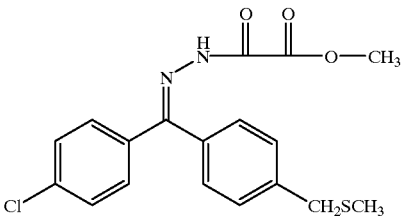
(VI)

A compound having the following formula (VII) is described in EP 742202:

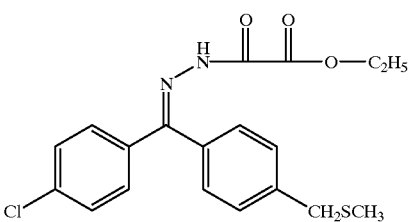
(VII)

However, the insecticidal activity of these compounds is not always high, and investigations have been made for the purpose of finding a compound having a higher insecticidal activity.

SUMMARY OF THE INVENTION

Accordingly, one object of the present invention is to provide a hydrazine oxoacetamide derivative or a salt thereof having an insecticidal activity higher than those of the ordinary insecticides.

A particular object of the present invention is to provide a hydrazine oxoacetamide derivative or a salt thereof having an excellent insecticidal effect on harmful insects of Lepidoptera and Coleoptera and also soil insect pests.

The present invention relates to a hydrazine oxoacetamide derivative having the following formula or a salt thereof:

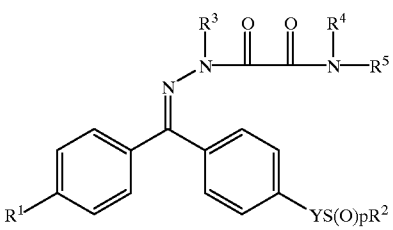
(I)

wherein
$R^1$ represents a chlorine atom or a bromine atom,
Y represents an oxygen atom or a methylene group, and when Y is an oxygen atom, p is 2 and when Y is a methylene group, p is 0,
$R^2$ represents a trifluoromethyl group,
$R^3$ represents a hydrogen atom or a methyl group,
$R^4$ represents a hydrogen atom or a methyl group, and
$R^5$ represents a methyl group, an ethyl group, an n-propyl group, a cyclopropyl group, an allyl group or a propargyl group.

DETAILED DESCRIPTION OF THE PREFERRED EMBODIMENTS

After intensive investigations on various hydrazine oxoacetamide derivatives in a wide range made for the purpose of developing compounds having an insecticidal activity higher than the activities of conventional hydrazine oxoacetamide derivatives, the inventors have found a new compound which is related to the conventional hydrazine oxoacetamide derivatives, which is represented by Formula (I) given above, and which has a high insecticidal activity. The present invention has been completed on the basis of this finding.

The hydrazine oxoacetamide derivative of the present invention is represented by the above Formula (I). The hydrazine oxoacetamide derivative of the present invention may be in the form of a geometrical isomer of syn- type and anti- type. The geometrical isomer may be in its pure form or a mixture of them. A salt of a hydrazine oxoacetamide derivative is also included in the present invention.

The salt is, for example, a salt with an alkali metal such as sodium and potassium and also with an alkaline earth metal such as magnesium and calcium.

Examples of the hydrazine oxoacetamide derivatives of the present invention include those compounds shown in the following Tables 1 and 2.

TABLE 1

(I)

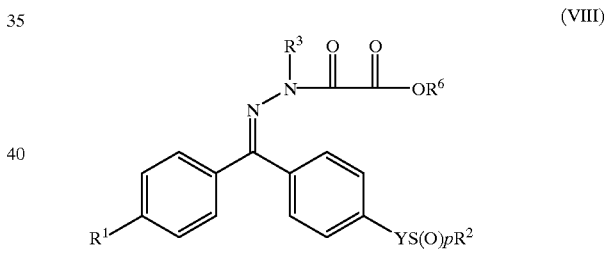

| Compound No. | $R^1$ | Y | p | $R^2$ | $R^3$ | $R^4$ | $R^5$ |
|---|---|---|---|---|---|---|---|
| 1-3 | Cl | O | 2 | $CF_3$ | H | H | $CH_3$ |
| 1-5 | Cl | O | 2 | $CF_3$ | H | H | $C_2H_5$ |
| 1-7 | Cl | O | 2 | $CF_3$ | H | H | n-$C_3H_7$ |
| 1-27 | Cl | O | 2 | $CF_3$ | H | H | $CH_2CH=CH_2$ |
| 1-37 | Cl | O | 2 | $CF_3$ | H | H | $CH_2C\equiv CH$ |
| 1-43 | Cl | O | 2 | $CF_3$ | H | H | c-$C_3H_5$ |
| 1-133 | Cl | O | 2 | $CF_3$ | H | $CH_3$ | $CH_3$ |
| 1-147 | Cl | O | 2 | $CF_3$ | H | $CH_3$ | c-$C_3H_5$ |
| 1-178 | Cl | O | 2 | $CF_3$ | $CH_3$ | H | $CH_3$ |
| 1-180 | Cl | O | 2 | $CF_3$ | $CH_3$ | H | $C_2H_5$ |
| 1-182 | Cl | O | 2 | $CF_3$ | $CH_3$ | H | n-$C_3H_7$ |
| 1-202 | Cl | O | 2 | $CF_3$ | $CH_3$ | H | $CH_2CH=CH_2$ |
| 1-212 | Cl | O | 2 | $CF_3$ | $CH_3$ | H | $CH_2C\equiv CH$ |
| 1-218 | Cl | O | 2 | $CF_3$ | $CH_3$ | H | c-$C_3H_5$ |
| 1-304 | Cl | O | 2 | $CF_3$ | $CH_3$ | $CH_3$ | $CH_3$ |
| 1-306 | Cl | O | 2 | $CF_3$ | $CH_3$ | $CH_3$ | $C_2H_5$ |
| 1-308 | Cl | O | 2 | $CF_3$ | $CH_3$ | $CH_3$ | n-$C_3H_7$ |
| 1-318 | Cl | O | 2 | $CF_3$ | $CH_3$ | $CH_3$ | c-$C_3H_5$ |
| 1-515 | Br | O | 2 | $CF_3$ | H | H | $CH_3$ |
| 1-517 | Br | O | 2 | $CF_3$ | H | H | $C_2H_5$ |
| 1-519 | Br | O | 2 | $CF_3$ | H | H | n-$C_3H_7$ |
| 1-555 | Br | O | 2 | $CF_3$ | H | H | c-$C_3H_5$ |
| 1-645 | Br | O | 2 | $CF_3$ | H | $CH_3$ | $CH_3$ |
| 1-647 | Br | O | 2 | $CF_3$ | H | $CH_3$ | $C_2H_5$ |
| 1-649 | Br | O | 2 | $CF_3$ | H | $CH_3$ | n-$C_3H_7$ |
| 1-672 | Br | O | 2 | $CF_3$ | $CH_3$ | H | $CH_3$ |
| 1-674 | Br | O | 2 | $CF_3$ | $CH_3$ | H | $C_2H_5$ |
| 1-676 | Br | O | 2 | $CF_3$ | $CH_3$ | H | n-$C_3H_7$ |
| 1-686 | Br | O | 2 | $CF_3$ | $CH_3$ | $CH_3$ | $CH_3$ |
| 1-688 | Br | O | 2 | $CF_3$ | $CH_3$ | $CH_3$ | $C_2H_5$ |
| 1-690 | Br | O | 2 | $CF_3$ | $CH_3$ | $CH_3$ | n-$C_3H_7$ |

Note) "n-" indicates --normal--, and "c-" indicates --cyclic--. The same shall apply hereinafter.

TABLE 2

(Formula (I))

| Comp. No. | $R^1$ | Y | p | $R^2$ | $R^3$ | $R^4$ | $R^5$ |
|---|---|---|---|---|---|---|---|
| 2-4 | Cl | $CH_2$ | 0 | $CF_3$ | H | H | $CH_3$ |
| 2-6 | Cl | $CH_2$ | 0 | $CF_3$ | H | H | $C_2H_5$ |
| 2-8 | Cl | $CH_2$ | 0 | $CF_3$ | H | H | n-$C_3H_7$ |
| 2-28 | Cl | $CH_2$ | 0 | $CF_3$ | H | H | $CH_2CH=CH_2$ |
| 2-38 | Cl | $CH_2$ | 0 | $CF_3$ | H | H | $CH_2C\equiv CH$ |
| 2-44 | Cl | $CH_2$ | 0 | $CF_3$ | H | H | c-$C_3H_5$ |
| 2-134 | Cl | $CH_2$ | 0 | $CF_3$ | H | $CH_3$ | $CH_3$ |
| 2-136 | Cl | $CH_2$ | 0 | $CF_3$ | H | $CH_3$ | $C_2H_5$ |
| 2-138 | Cl | $CH_2$ | 0 | $CF_3$ | H | $CH_3$ | n-$C_3H_7$ |
| 2-155 | Cl | $CH_2$ | 0 | $CF_3$ | $CH_3$ | H | $CH_3$ |
| 2-157 | Cl | $CH_2$ | 0 | $CF_3$ | $CH_3$ | H | $C_2H_5$ |
| 2-159 | Cl | $CH_2$ | 0 | $CF_3$ | $CH_3$ | H | n-$C_3H_7$ |
| 2-163 | Cl | $CH_2$ | 0 | $CF_3$ | $CH_3$ | $CH_3$ | $CH_3$ |
| 2-165 | Cl | $CH_2$ | 0 | $CF_3$ | $CH_3$ | $CH_3$ | $C_2H_5$ |
| 2-167 | Cl | $CH_2$ | 0 | $CF_3$ | $CH_3$ | $CH_3$ | n-$C_3H_7$ |
| 2-202 | Br | $CH_2$ | 0 | $CF_3$ | H | H | $CH_3$ |
| 2-204 | Br | $CH_2$ | 0 | $CF_3$ | H | H | $C_2H_5$ |
| 2-206 | Br | $CH_2$ | 0 | $CF_3$ | H | H | n-$C_3H_7$ |
| 2-218 | Br | $CH_2$ | 0 | $CF_3$ | H | H | $CH_2CH=CH_2$ |
| 2-224 | Br | $CH_2$ | 0 | $CF_3$ | H | H | $CH_2C\equiv CH$ |
| 2-226 | Br | $CH_2$ | 0 | $CF_3$ | H | H | c-$C_3H_5$ |

Then, the description will be made on the processes for producing the hydrazine oxoacetamide derivative or salts thereof.

Production Process A

The hydrazine oxoacetamide derivatives of the present invention represented by Formula (I) can be easily produced by reacting a compound (VIII) represented by Formula (VIII):

(VIII)

wherein $R^1$, Y, p, $R^2$ and $R^3$ are the same as defined above, and $R^6$ represents an alkyl group, preferably a linear or branched alkyl group having 1 to 6 carbon atoms, particularly preferably 1 or 2 carbon atoms; preferred examples thereof being a methyl group, an ethyl group, an n-propyl group, an isopropyl group, an n-butyl group, an isobutyl group, an s-butyl group, a t-butyl group, an n-pentyl group, an isopentyl group, an s-pentyl group, a t-pentyl group, a neopentyl group, an n-hexyl group, an isohexyl group, an s-hexyl group, a t-hexyl group and a neohexyl group with a compound (IX) represented by Formula (IX):

(IX)

wherein $R^4$ and $R^5$ are the same as defined above.

Production Process B

The compound represented by Formula (I) can be easily produced by reacting a compound (X) represented by Formula (X):

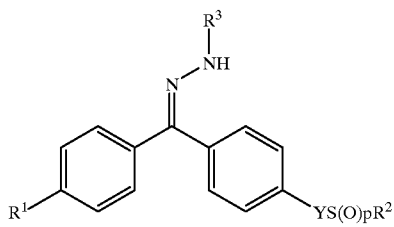

(X)

wherein $R^1$, Y, p, $R^2$ and $R^3$ are the same as defined above, with a compound (XI) represented by Formula (XI):

(XI)

wherein X represents a chlorine or bromine atom, and $R^4$ and $R^5$ are the same as defined above, in the presence of a base, if necessary.

Production Process C

The compound represented by Formula (I), wherein $R^1$, Y, p, $R^2$, $R^3$, $R^4$ and $R^5$ are the same as defined above, can be easily produced by reacting a compound, represented by Formula (IX) wherein at least one of $R^3$, $R^4$ and $R^5$ represents a hydrogen atom, with a compound (XII) of Formula (XII):

 (XII)

wherein X represents a halogen atom (such as a chlorine atom) and $R^7$ represents a methyl group, an ethyl group, an n-propyl group, a cyclopropyl group, an allyl group or a propargyl group,
or a compound (XIII) of Formula (XIII):

 (XIII)

wherein $R^8$ represents a methyl group, an ethyl group or the like as described above, in the presence of a base, if necessary.

As for Production Process A

When the starting materials are, for example, methyl {N'-[(4-chlorophenyl)-(4-trifluoromethanesulfonyloxyphenyl)-methylene] hydrazino}-oxo-acetate and ethylamine, the reaction is shown by the following reaction formula (1):

Reaction formula (1):

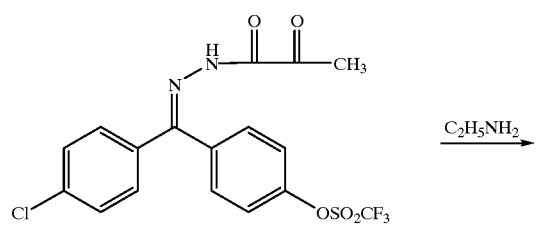

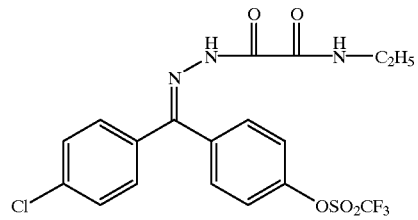

Examples of the compounds (VIII) usable as the starting material in the above-described process are shown in Table 3 below.

TABLE 3

| Intermediate No. | $R^1$ | Y | p | $R^2$ | $R^3$ | $R^6$ | Literature |
|---|---|---|---|---|---|---|---|
| 5-2 | Cl | O | 2 | $CF_3$ | H | $CH_3$ | J.P. Kokai Hei 10-67732 |
| 5-4 | Cl | O | 2 | $CF_3$ | H | $C_2H_5$ | |
| 5-6 | Cl | O | 2 | $CF_3$ | $CH_3$ | $CH_3$ | |
| 5-8 | Cl | O | 2 | $CF_3$ | $CH_3$ | $C_2H_5$ | EP-662472 |
| 5-16 | Br | O | 2 | $CF_3$ | H | $CH_3$ | |
| 5-18 | Br | O | 2 | $CF_3$ | H | $C_2H_5$ | |
| 5-20 | Br | O | 2 | $CF_3$ | $CH_3$ | $CH_3$ | |
| 5-22 | Br | O | 2 | $CF_3$ | $CH_3$ | $C_2H_5$ | |
| 5-28 | Cl | $CH_2$ | 0 | $CF_3$ | H | $CH_3$ | |
| 5-30 | Cl | $CH_2$ | 0 | $CF_3$ | H | $C_2H_5$ | |
| 5-32 | Cl | $CH_2$ | 0 | $CF_3$ | $CH_3$ | $CH_3$ | |
| 5-34 | Cl | $CH_2$ | 0 | $CF_3$ | $CH_3$ | $C_2H_5$ | |
| 5-42 | Br | $CH_2$ | 0 | $CF_3$ | H | $CH_3$ | |
| 5-44 | Br | $CH_2$ | 0 | $CF_3$ | H | $C_2H_5$ | |
| 5-46 | Br | $CH_2$ | 0 | $CF_3$ | $CH_3$ | $CH_3$ | |
| 5-48 | Br | $CH_2$ | 0 | $CF_3$ | $CH_3$ | $C_2H_5$ | |
| 5-54 | Cl | $CH_2$ | 1 | $CF_3$ | H | $CH_3$ | |
| 5-56 | Cl | $CH_2$ | 1 | $CF_3$ | H | $C_2H_5$ | |
| 5-58 | Cl | $CH_2$ | 1 | $CF_3$ | $CH_3$ | $CH_3$ | |
| 5-60 | Cl | $CH_2$ | 1 | $CF_3$ | CH3 | $C_2H_5$ | |

Some of the compounds in the above Table 3 are known compounds. They are described in, for example, J. P. Kokai No. Hei 10-67732 and EP-662472. The other compounds can be easily produced by the processes shown in the above-described official gazettes.

The compounds of Formula (IX) are known compounds which can be easily produced and which are easily available on the market.

The compounds of Formula (IX) are usable in the form of either free compounds or salts thereof. When they are used in the form of the salts, suitable bases can be used as deacidifying agents, if necessary. Examples of these bases include pyridine, triethylamine, potassium carbonate, potassium hydrogencarbonate, sodium carbonate, sodium hydrogencarbonate, potassium hydroxide, sodium hydroxide, sodium methylate, potassium tert-butoxide, sodium hydride and potassium hydride. The reaction can be carried out in a suitable diluent. Any diluent can be used so long as it per se does not inhibit the reaction. The diluents are aliphatic or aromatic hydrocarbons such as pentane, hexane, cyclohexane, petroleum ether, ligroine, benzene, toluene, xylene, dichloromethane, chloroform, carbon tetrachloride, 1,2-dichloroethane and chlorobenzene; ethers such as ethyl ether, methyl ethyl ether, isopropyl ether, butyl ether, tetrahydrofuran, dioxane and dimethoxyethane; nitriles such as acetonitrile, propionitrile and acrylonitrile; alcohols such as methanol, ethanol, isopropanol, n-butanol and ethylene glycol; acid amides such as dimethylformamide, dimethylacetamide and N-methylpyrrolidone; sulfoxides such as dimethyl sulfoxide and sulfolane; and bases such as triethylamine and pyridine. The reaction can be carried out at a temperature in a substantially wide range. However, the reaction temperature is usually in the range of about −30 to about 150, preferably in the range of 0 to about 130. Although the reaction is desirably carried out under atmospheric pressure, it can be carried out also under elevated pressure or reduced pressure, if necessary. In this process, for example, 1 mole of a compound of Formula (VIII) can be reacted with 1 to 1.5 moles of a compound of Formula (IX) in a diluent such as ethanol.

As for Production Process B

When the starting materials are, for example, 4-[(4-chlorophenyl)hydrazonomethyl]phenyl trifluoromethanesulfonate and N-ethyloxamoyl chloride, the reaction is shown by the following reaction formula (2):

Reaction formula (2):

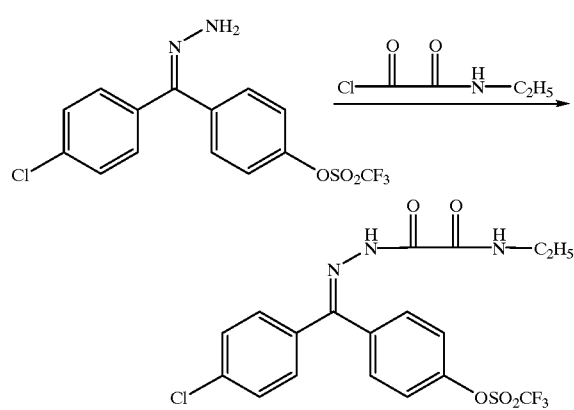

Examples of the compounds (X) usable as the starting material in the above-described process are shown in Table 4 below.

TABLE 4

| Intermediate No. | $R^1$ | Y | p | $R^2$ | $R^3$ | Literature |
|---|---|---|---|---|---|---|
| 6-2 | Cl | O | 2 | $CF_3$ | H | EP-26040 |
| 6-4 | Cl | O | 2 | $CF_3$ | $CH_3$ | EP-662472 |
| 6-8 | Br | O | 2 | $CF_3$ | H | |
| 6-10 | Br | O | 2 | $CF_3$ | $CH_3$ | |
| 6-16 | Cl | $CH_2$ | 0 | $CF_3$ | H | WO 96/33168 |
| 6-18 | Cl | $CH_2$ | 0 | $CF_3$ | $CH_3$ | |
| 6-22 | Br | $CH_2$ | 0 | $CF_3$ | H | |
| 6-24 | Br | $CH_2$ | 0 | $CF_3$ | $CH_3$ | |
| 6-30 | Cl | $CH_2$ | 1 | $CF_3$ | H | WO 96/33168 |
| 6-32 | Cl | $CH_2$ | 1 | $CF_3$ | $CH_3$ | |
| 6-36 | Br | $CH_2$ | 1 | $CF_3$ | H | |
| 6-38 | Br | $CH_2$ | 1 | $CF_3$ | $CH_3$ | |
| 6-44 | Cl | $CH_2$ | 2 | $CF_3$ | H | WO 96/33168 |
| 6-46 | Cl | $CH_2$ | 2 | $CF_3$ | $CH_3$ | |
| 6-50 | Br | $CH_2$ | 2 | $CF_3$ | H | WO 96/33168 |
| 6-52 | Br | $CH_2$ | 2 | $CF_3$ | $CH_3$ | |

Some of the compounds in the above Table 4 are known. They are shown in, for example, EP-26040, EP-662472, WO 96/33168 and WO 97/11050. The other compounds can be easily produced by the processes shown in the above-described official gazettes.

The compounds of Formula (X) are usable in the form of either free compounds or salts thereof. When they are used in the form of the salts, suitable bases can be used as the deacidifying agents. Examples of these bases include pyridine, triethylamine, potassium carbonate, potassium hydrogencarbonate, sodium carbonate, sodium hydrogencarbonate, potassium hydroxide, sodium hydroxide, sodium methylate, potassium tert-butoxide, sodium hydride and potassium hydride.

The compounds (XI) can be easily produced by, for example, the process described in J. Org. Chem., 48, pp. 4111 to 4113 (1983). If necessary, a base can be used for the reaction. The bases are the same as those described above with reference to production process A.

The reaction can be carried out in a suitable diluent. Any diluent can be used so far as it per se does not inhibit the reaction. The diluent is those listed above and, in addition, esters such as ethyl acetate.

The reaction can be carried out at a temperature in a substantially wide range. However, the reaction temperature is usually in the range of about −30 to about 150, preferably in the range of 0 to about 100. Although the reaction is desirably carried out under atmospheric pressure, it can be carried out also under elevated pressure or reduced pressure, if necessary. In this process, for example, 1 mole of the compound of Formula (X) can be reacted with 1 to 1.5 moles of the compound of Formula (XI) in a diluent such as tetrahydrofuran to obtain an intended compound.

As for Production Process C

When the starting materials are, for example, 4-[(4-chlorophenyl)-(ethylaminooxalyl-hydrazono)methyl]-phenyl trifluoromethanesulfonate and methyl iodide, the reaction is shown by the following reaction formula (3):

Reaction formula (3):

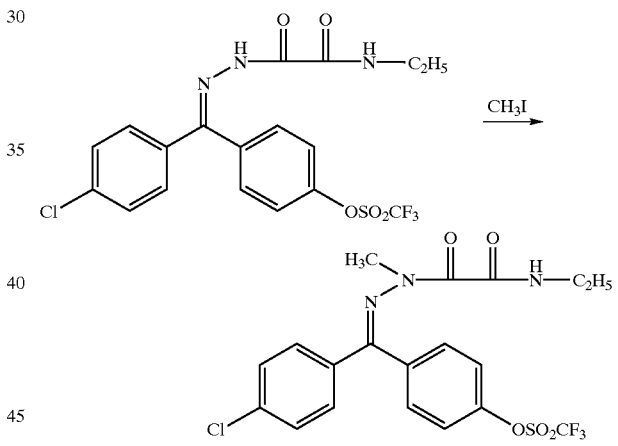

Examples of the compounds of Formula (XII) usable for introducing a substituent into $R^3$ of the starting material of Formula (I) wherein $R^3$ is a hydrogen atom include alkyl halides such as methyl iodide and methyl bromide. The compounds of Formula (XIII) are, for example, alkyl sulfates such as dimethyl sulfate and diethyl sulfate.

The compounds of Formula (XII) usable for introducing a substituent into $R^4$ or $R^5$ of the starting material of Formula (I) wherein $R^3$ is a methyl group and $R^4$ or $R^5$ is hydrogen atoms are, for example, alkyl halides such as methyl iodide, methyl bromide and n-propyl iodide; alkenyl halides such as allyl bromide; and alkynyl halides such as propargyl bromide. The compounds of Formula (XIII) include alkyl sulfates such as dimethyl sulfate and diethyl sulfate.

The compounds of Formulae (XII) and (XIII) are known compounds which can be easily produced and which are easily available on the market. A base is usable, if necessary, for the reaction. The bases are the same as those described above with reference to production process A.

The reaction can be carried out in a suitable diluent. Any diluent is usable herein so far as itper se does not inhibit the reaction. The diluent is those listed above with reference to production process B.

The reaction can be carried out at a temperature in a substantially wide range. However, the reaction temperature is usually in the range of about −30 to about 150, preferably in the range of 0 to about 100. Although the reaction is desirably carried out under atmospheric pressure, it can be carried out also under elevated pressure or reduced pressure, if necessary. In this process, for example, 1 mole of the compound of Formula (I) can be reacted with 1 to 4 moles of the compound of Formula (XII) or (XIII) in a diluent such as N,N-dimethylformamide to obtain an intended compound.

In the above-described reaction, the substituents can be introduced into $R^3$, $R^4$ and $R^5$ in one to three steps.

The hydrazine oxoacetamide derivative of Formula (I) and a salt thereof of the present invention exhibits an insecticidal effect stronger than those of the conventional insecticides.

The hydrazine oxoacetamide derivative of Formula (I) or a salt thereof of the present invention, even at an extremely low concentration, exhibits an insecticidal effect on various harmful insect pests. The harmful insect pests include, for example, lepidopterons such as cabbage army worms (*Mamestra brassicae*), common cabbage worms (*Pieris rapae crucivora*), diamond back moth (*Plutella xylostera*), beet semi-looper (*Autographa nigrisigna*), leaf folders (e.g. *Archips xylosteanus*) and rice borers; the order of beetles such as scarab beetles, leaf beetles, 28-spotted lady beetles (*Epilachna sparsa orientalis*) and rice water weevil (*Lissorhoptrus oryzophilus*); insects of Hemiptera such as planthoppers, leaf hoppers, white flies, aphides and coccidia; and thrips such as yellow tea thrips (*Scirtothrips dorsalis*) and Thrips palmi; sanitary insect pests such as mosquitoes, flies, cockroaches, fleas and lice, stored grain insect pests, clothes moths, house insect pests, plant parasitic nematodes such as root-knot nematodes and root-lesion nematodes (*Pratylenchus paratensis*); and plant parasitic spider mites such as two-spotted spider mite (*Tetranychus urticae*), kanzawa spider mite (*Tetranychus kanzawai*) and citrus red mite (*Panonychus citri*). The insecticides of the present invention are particularly effective on Lepidoptera such as Tobacco cutworm (*Prodenia litura*), cabbage armyworm (*Mamestra brassicae*) and diamond backmoth (*Pluttella xylostera*). They are also effective on soil insect pests. The term "soil insect pests" herein include gastropods such as slugs and snails; and wood lice (isopods) such as pill bugs and sow bugs. Further, they are effective on plant parasitic spider mites which are resistant to Dicofol and organophosphorus pesticides, and aphids and houseflies resistant to organophosphorus pesticides.

The hydrazine oxoacetamide derivative or its salt of the present invention exhibits a remarkable insecticidal effect on the above-described insect pests which damage lowland crops, upland crops, fruit trees, vegetables and other crops as well as ornamental plants. The insecticidal effects of the compounds of the present invention are exhibited by treating water in paddy fields, foliages, soil, seeds and bulbs in paddy fields, upland fields, fruit trees, vegetables and ornamental plants before or after the insect pest generation is estimated in a season in which the pest breed is supposed.

The dosage of the hydrazine oxoacetamide derivative or its salt of the present invention cannot be generally prescribed because it varies depending on the crops to be treated, method of the application, formulation and dose. In the foliar treatment, the active ingredient is used in an amount of, for example, 0.1 to 10,000 ppm, desirably 1 to 2,000 ppm.

The hydrazine oxoacetamide derivative or its salt of the present invention can be formulated in an ordinary form.

As for the formulation, the present compound can be mixed with, for example, a dust, solid carrier, solvent, surfactant and other formulation assistants into a form of an emulsion, aqueous solution, microemulsion, wettable powder, aqueous or oily suspension, wettable granules, water-soluble powder, microcapsules or the like. The hydrazine oxoacetamide derivative or its salt of the present invention is contained as an active ingredient in the preparations in an amount of, for example, 0.002 to 80% by weight, preferably 0.01 to 70% by weight.

The solid carrier includes kaolin clay, attapulgite clay, bentonite, acid clay, pyrophyllite, talc, diatomaceous earth, calcite, walnut starch, urea, ammonium sulfate, synthetic silicic acid hydrate, etc.

The solvent covers aromatic and aliphatic hydrocarbons such as xylene, naphthas, methylnaphthalene, paraffins and machine oils; alcohols such as isopropanol, butanol, propylene glycol, ethylene glycol, cellosolve and carbitol; ketones such as acetone, cyclohexanone and isophorone; vegetable oils such as soybean oil and cotton seed oil; dimethyl sulfoxide; N,N-dimethylformamide; N-methylpyrrolidone; acetonitrile; and water.

The surfactants used for emulsification, dispersion, wetting or the like include anionic surfactants such as lignin sulfonates, alkylnaphthalenesulfonates, naphthalenesulfonates/formaldehyde condensates, alkylsulfates, alkylsulfonates, alkylarylsulfonates, dialkylsulfosuccinates, polyoxyethylene alkylaryl ether sulfates (sulfonates or phosphates), polyoxyethylene alkyl ether sulfates (phosphates or sulfonates), and polyoxyethylene styrenated and benzylated phenyl ether phosphoric acid or phosphates (sulfates, sulfonates); and nonionic surfactants such as polyoxyethylene alkyl ethers, polyoxyethylene alkylaryl ethers, polyoxyethylene fatty acid esters, polyoxyethylene/polyoxypropylene block copolyrners, sorbitan fatty acid esters, polyoxyethylene sorbitan fatty acid esters, and polyoxyethylene styrenated or benzylated phenyl ethers.

Other adjuvants include alginates, polyvinyl alcohols, acacia gum, carboxymethylcellulose, Xantham gum, Welan gum, isopropyl hydrogen phosphate, etc.

The wettable powder which is a typical example of the preparations can be prepared by mixing and pulverizing, for example, about 5 to 50 parts by weight of the hydrazine oxoacetamide derivative of the present invention or its salt, 2 to 5 parts by weight of the anionic surfactant and the solid carrier in an amount sufficient for making the total amount 100 parts by weight.

The dust can be prepared by mixing, for example, about 0.01 to 10 parts by weight of the present hydrazine oxoacetamide derivative or its salt, 0.1 to 0.5 part by weight of the wetting agent and a fine mineral powder selected from among the solid carriers.

The emulsion can be prepared by mixing, for example, 1 to 70 parts by weight of the hydrazine oxoacetamide derivative or the salt thereof of the present invention, 5 to 15 parts by weight of the nonionic surfactant, 1 to 10 parts by weight of the anionic surfactant and an inert, pharmaceutically acceptable liquid diluent in an amount sufficient for making the total amount 100 parts by weight.

The aqueous suspension can be prepared by mixing, for example, 5 to 50 parts by weight of the present hydrazine oxoacetamide derivative or its salt, 1 to 5 parts by weight of the nonionic surfactant or the anionic surfactant and water in an amount sufficient for making the total amount 100 parts by weight, wet-pulverizing the mixture until a particle size of 0.1 to 3 µm, preferably 0.5 to 2 µm, is obtained, and then mixing the obtained mixture with 0.1 to 1 part by weight of thickener.

The wettable granules are in the form of granules comprising, for example, 5 to 50 parts by weight of the present hydrazine oxoacetamide derivative or its salt, 90 to 40 parts by weight of an inorganic salt selected from among solid carriers and/or a fine mineral powder, 0.1 to 5 parts by weight of a binder and 5 to 10 parts by weight of a surfactant. When the wettable granules are fed into water, they are rapidly disintegrated and dispersed therein.

The present hydrazine oxoacetamide derivative or its salt can be used in the form of a mixture with, or in combination with, other pesticides such as insecticides, acaricides, nematocides, germicides, antiviral agents, attractants, herbicides, plant growth regulators, etc., if necessary. In such a case, a more excellent effect can be expected.

The compounds usable as active ingredients of the above-described insecticides, acaricides and nematicides include, for example, the following compounds:

organophosphoric ester compounds such as O-(4-bromo-2-chlorophenyl) O-ethyl-S-propylphosphorothioate (common name: Profenofos), O-(2,2-dichlorovinyl) O,O-dimethylphosphate (common name: Dichlorvos), O-ethyl O-[3-methyl-4-(methylthio)phenyl] N-isopropylphosphoroamidate (common name: Fenamiphos), O,O-dimethyl O-(4-nitro-m-tolyl) phosphorothioate (common name: Fenitrothion), O-ethyl O-(4-nitrophenyl)phenylphosphonothioate (common name: EPN), O,O-diethyl O-(2-isopropyl-6-methylpyrimidine-4-yl)phosphorothioate (common name; Diazinon), O,O-dimethyl O-(3,5,6-trichloro-2-pyridyl)phosphorothioate (common name: Chlorpyrifos-methyl), O,S-dimethyl N-acetylphosphoroamidothioate (common name: Acephate), O-(2,4-dichlorophenyl), O-ethyl S-propylphosphorodithioate (common name: Prothiofos) and (RS)-S-sec-butyl O-ethyl 2-oxo-1,3-thiazolidine-3-ylphosphonothioate (common name: Fosthiazate);

carbamate compounds such as 1-naphthyl N-methylcarbamate (common name: Carbaryl), 2-isopropoxyphenyl N-methylcarbamate (common name: Propoxur) 2-methyl-2-(methylthio)propionaldehyde O-methylcarbamoyloxime (common name: Aldicarb), 2,3-dihydro-2,2-dimethylbenzofuran-7-yl N-methylcarbamate (common name: Carbofuran), dimethyl N,N'-[thiobis (methylimino)carbonyloxy)]bisethanimidothioate (common name: Thiodicarb), S-methyl N-(methylcarbamoyloxy) thioacetimidate (common name: Methomyl), N,N-dimethyl-2-methylcarbamoyloxyimino-2-(methylthio)acetamide (common name: Oxamyl), 2-(ethylthiomethyl)phenyl N-methylcarbamate (common name; Ethiofencarb), 2-dimethylamino-5,6-dimethylpyrimidine-4-yl N,N-dimethylcarbamate (common name: Pirimicarb) and 2-sec-butylphenyl N-methylcarbamate (common name: Fenobucarb);

Nereistoxin derivatives such as S,S'-2-dimethylaminotrimethylene bis(thiocarbamate) (common name: Cartap) and N,N-dimethyl-1,2,3-trithian-5-ylamine (common name: Thiocyclam);

organochlorine compounds such as 2,2,2-trichloro-1,1-bis (4-chlorophenyl)ethanol (common name: Dicofol) and 4-chlorophenyl-2,4,5-trichlorophenyl sulfone (common name: Tetradifon);

organometallic compounds such as bis[tris(2-methyl-2-phenylpropyl)tin] oxide (common name: Fenbutatin Oxide);

pyrethroid compounds such as (RS)-α-cyano-3-phenoxybenzyl(RS)-2-(4-chlorophenyl)-3-methylbutyrate (common name: Fenvalerate), 3-phenoxybenzyl(1RS)-cis, trans-3-(2,2-dichlorovinyl)-2,2-dimethylcyclopropanecarboxylate (common name: Permethrin), (RS)-α-cyano-3-phenoxybenzyl(1RS)-cis, trans-3-(2,2-dichlorovinyl)-2,2-dimethylcyclopropanecarboxylate (common name: Cypermethrin), (S)-α-cyano-3-phenoxybenzyl(1R)-cis-3-(2,2-dibromovinyl)-2,2-dimethylcyclopropanecarboxylate (common name: Deltamethrin), (RS)-α-cyano-3-phenoxybenzyl(1RS)-cis,trans-3-(2-chloro-3,3,3-trifluoropropenyl)-2,2-dimethylcyclopropanecarboxylate (common name: Cyhalothrin), 4-methyl-2,3,5,6-tetrafluorobenzyl-3-(2-chloro-3,3,3-trifluoro-1-propenyl)-2,2-dimethylcyclopropanecarboxylate (common name: Tefluthrin) and 2-(4-ethoxyphenyl)-2-methylpropyl-3-phenoxybenzyl ether (common name: Ethofenprox);

benzoylurea compounds such as 1-(4-chlorophenyl)-3-(2,6-difluorobenzoyl)urea (common name: Diflubenzuron), 1-[3,5-dichloro-4-(3-chloro-5-trifluoromethyl-2-pyridyloxy)phenyl]-3-(2,6-difluorobenzoyl)urea (common name: Chlorfluazuron), 1-(3,5-dichloro-2,4-difluorophenyl)-3-(2,6-difluorobenzoyl)urea (common name: Teflubenzuron);

juvenile hormone-like compounds such as isopropyl (2E, 4E)- 1-methoxy-3,7,11-trimethyl-2,4-dodecadienoate (common name: Methoprene);

pyridazinone compounds such as 2-t-butyl-5-(4-t-butylbenzylthio)-4-chloro-3(2H)-pyridazinone (common name: Pyridaben);

pyrazole compounds such as t-butyl 4-[(1,3-dimethyl-5-phenoxypyrazole-4-yl)methyleneaminoxymethyl]benzoate (common name: Fenpyroximate);

nitro compounds such as 1-(6-chloro-3-pyridylmethyl)-N-nitroimidazolidine-2-ylideneamine (common name: Imidacloprid), 1-[N-(6-chloro-3-pyridylmethyl)-N-ethylamino]-1-methylamino-2-nitroethylene (European Patent Publication No. 302389), 2-methylamino-2-[N-methyl-N-(6-chloro-3-pyridylmethyl)amino]-1-nitroethylene (European Patent Publication No. 302389), 1-(6-chloro-3-pyridylmethyl)amino-1-dimethylamino-2-nitroethylene (European Patent Publication No. 302389), 1-(6-chloro-3-pyridylmethyl)-2-(1-nitro-2-allylthioethylidene)imidazolidine (European Patent Publication No. 437784), 1-(6-chloro-3-pyridylmethyl)-2-(1-nitro-2-ethylthioethylidene)imidazolidine (European Patent Publication No. 437784), 1-(6-chloro-3-pyridylmethyl)-2-(1-nitro-2-β-methylallylthioethylidene)imidazolidine (European Patent Publication No. 437784), 1-(6-chloro-3-pyridylmethyl)-3-methyl-2-nitroguanidine (European Patent Publication No. 383091), 1-(6-chloro-3-pyridylmethyl)-3,3-dimethyl-2-nitroguanidine (European Patent Publication No. 383091), 3-(6-chloro-3-pyridylmethyl)-2-nitromethylene-thiazolidine (European Patent Publication No. 192060), 1-(6-chloro-3-pyridylmethyl)-2-(nitromethylene)imidazolidine (European Patent Publication No. 163855), 6-(6-chloro-3-pyridylmethylamino)-1,3-dimethyl-5-nitro-1,2,3,4-tetrahydropyrimidine (European Patent Publication No. 366085) and 1-(6-chloro-3-pyridylmethyl)-5-nitro-3-methyl-6-methylamino-1,2,3,4-tetrahydropyrimidine (European Patent Publication No. 366085);

dinitro compounds, organosulfur compounds, urea compounds, triazine compounds, hydrazine compounds and other compounds such as 2-tert-butylimino-3-isopropyl-5-phenyl-3,4,5,6-tetrahydro-2H-1,3,5-thiadiazine-4-on (common name: Buprofezin), trans-(4-chlorophenyl)-N-cyclohexyl-4-methyl-2-oxothiazolidinone-3-carboxamide (common name: Hexythiazox), N-methylbis(2,4-xylyliminomethyl)amine (common name: Amitraz), N'-(4-chloro-o-tolyl)-N,N-dimethylformamidine (common name: Chlordimeform) and (4-ethoxyphenyl)-[3-(4-fluoro-3-phenoxyphenyl)propyl](dimethyl)silane (common name: Silafluofen). Further, the compounds of the present invention may also be used in mixture or combination with microbial pesticides such as BT and insect pathogenic viruses, and also antibiotics such as avermectin and milbemycin.

Compounds usable as the active ingredients of the fungicides include pyrimidinamine compounds such as 2-anilino-4-methyl-6-(1-propinyl)pyrimidine (common name: Mepanipyrim) and 4,6-dimethyl-N-phenyl-2-pyrimidinamine (common name: Pyrimethanil);

azole compounds such as 1-(4-chlorophenoxy)-3,3-dimethyl-1-(1H-1,2,4-triazole-1y)butanone (common name: Triadimefon), 1-(biphenyl-4-yloxy)-3,3-dimethyl-1-(1H,1,2,4-triazole-1-yl)butane-2-ol (common name: Bitertanol), 1-[N-(4-chloro-2-trifluoromethylphenyl]-2-propoxyacetimidoyl]imidazole (common name: Triflumizole), 1-[2-(2,4-dichlorophenyl)-4-ethyl-1,3-dioxolane-2-ylmethyl]-1H-1,2,4-triazole (common name: Etaconazole), 1-[2-(2,4-dichlorophenyl)-4-propyl-1,3-dioxolane-2-ylmethyl]-1H-1,2,4-triazole (common name: Propiconazole), 1-[2-(2,4-dichlorophenyl)pentyl]-1H-1,2,4-triazole (common name: Penconazole), bis(4-fluorophenyl)(methyl)(1H-1,2,4-triazole-1-ylmethyl)silane (common name: Flusilazole), 2-(4-chlorophenyl)-2-(1H, 1,2,4-triazole-1-ylmethyl)hexanenitrile (common name: Myclobutanil), (2RS,3RS)-2-(4-chlorophenyl)-3-cyclopropyl-1-(1H-1,2,4-triazole-1-yl)butane-2-ol (common name: Cyproconazole), (RS)-1-(4-chlorophenyl)-4,4-dimethyl-3-(1H-1,2,4-triazole-1-ylmethyl)pentane-3-ol (common name: Terbuconazole), (RS)-2-(2,4-dichlorophenyl)-1-(1H-1,2,4-triazole-1-yl)hexane-2-ol (common name: Hexaconazole), (2RS,5RS)-5-(2,4-dichlorophenyl)tetrahydro-5-(1 H-1,2,4-triazole-1-ylmethyl)-2-furyl 2,2,2-trifluoroethyl ether (common name: Furconazole-cis) and N-propyl-N-[2-(2,4,6-trichlorophenoxy)ethyl]imidazole-1-carboxamide (common name: Prochloraz);

quinoxaline compounds such as 6-methyl-1,3-dithiolo[4,5-b]quinoxaline-2-on (common name: Quinomethionate);

dithiocarbamate compounds such as manganese ethylene bis(dithiocarbamate) polymer (common name: maneb), zinc ethylene bis(dithiocarbamate) polymer (common name: zineb), complex of zinc with manganese ethylene bis(dithiocarbamate) (maneb) (common name: Mancozeb), dizinc bis(dimethyldithiocarbamato)ethylene bis(dithiocarbamate) (common name: Polycarbamate) and zinc propylene bis(dithiocarbamate) polymer (common name: Propineb);

organochlorine compounds such as 4,5,6,7-tetrachlorophthalide (common name: Fthalide), tetrachloroisophthalonitrile (common name: Chlorothalonil) and pentachloronitrobenzene (common name: Quintozene);

benzimidazole compounds such as methyl 1-(butylcarbamoyl)benzimidazole-2-yl carbamate (common name: Benomyl), dimethyl 4,4'-(o-phenylene)bis(3-thioallophanate) (common name: Thiophnate-Methyl) and methyl benzimidazole-2-ylcarbamate (common name: Carbendazim);

Pyridinamine compounds such as 3-chloro-N-(3-chloro-2,6-dinitro-4-α,α,α-trifluorotolyl)-5-trifluoromethyl-2-pyridinamine (common name: Fluazinam); cyanoacetamide compounds such as 1-(2-cyano-2-methoxyiminoacetyl)-3-ethylurea (common name: Cymoxanil);

phenylamide compounds such as methyl N-(2-methoxyacetyl)-N-(2,6-xylyl)-DL-alaninate (common name: Metalaxyl), 2-methoxy-N-(2-oxo-1,3-oxazolidine-3-yl)aceto-2',6'-xylidide (common name: Oxadixyl), (±)-α-2-chloro-N-(2,6-xylylacetamido)-γ-butyrolactone (common name: Ofurace), methyl N-phenylacetyl-N-(2,6-xylyl)-DL-alaninate (common name: Benalaxyl), methyl N-(2-furoyl)-N-(2,6-xylyl)-DL-alaninate (common name: Furalaxyl) and (±)-α-[N-(3-chlorophenyl)cyclopropanecarboxamido]-γ-butyrolactone (common name: Cyprofuram); sulfenic acid compounds such as N-dichlorofluoromethylthio-N',N'-dimethyl-N-phenylsulfamide (common name: Dichlofluanid);

copper compounds such as cupric hydroxide (common name: cupric hydroxide) and copper 8-quinolinolate (common name: Oxine-Copper); isoxazole compounds such as 5-methylisoxazole-3-ol (common name: Hydroxyisoxazole);

organophosphorus compounds such as aluminum tris (ethylphosphonate) (common name: Fosetyl-aluminum), O-2,6-dichloro-p-tolyl-O,O-dimethylphosphorothioate (common name: Tolcofos-methyl), S-benzyl O,O-diisopropyl phosphorothioate, O-ethyl S,S-diphenylphosphorodithioate and aluminum ethyl hydrogenphosphonate;

N-halogenothioalkyl compounds such as N-(trichloromethylthio)cyclohex-4-en-1,2-dicarboximide (common name: Captan), N-(1,1,2,2-tetrachloroethylthio)cyclohex-4-en-1,2-dicarboximide (common name: Captafol) and N-(trichloromethylthio)phthalimide (common name: Folpet);

dicarboxyimide compounds such as N-(3,5-dichlorophenyl)-1,2-dimethylcyclopropane-1,2-dicarboximide (common name: Procymidone), 3-(3,5-dichlorophenyl)-N-isopropyl-2,4-dioxoimidazolidine-1-carboxamide (common name: Iprodione) and (RS)-3-(3,5-dichlorophenyl)-5-methyl-5-vinyl-1,3-oxazolidine-2,4-dion (common name: Vinclozlin);

benzanilide compounds such as α,α,α-trifluoro-3'-isopropoxy-o-toluanilide (common name: Flutolanil) and 3'-isopropoxy-o-toluanilide (common name: Mepronil);

benzamide compounds such as 2-(1,3-dimethylpyrazole-4-ylcarbonylamino)-4-methyl-3-pentenenitrile (a compound described in British Patent No. 2,190,3475) and α-(nicotinylamino)-(3-fluorophenyl)acetonitrile (a compound described in J.P. KOKAI No. Sho 63-135364);

piperazine compounds such as N,N'-[piperazine-1,4-diylbis(trichloromethyl)methylene]diformamide (common name: Triforine); pyridine compounds such as 2',4'-dichloro-2-(3-pyridyl)acetophenone O-methyloxime (common name: Pyrifenox);

carbinol compounds such as (±)-2,4'-dichloro-α-(pyrimidine-5-yl)benzhydryl alcohol (common name: Fenarimol), (±)-2,4'-difluoro-α-(1H- 1,2,4-triazole-1-ylmethyl)benzhydryl alcohol (common name: Flutriafol);

piperidine compounds such as (RS)-1-[3-(4-tert-butylphenyl)-2-methylpropyl]piperidine (common name: Fenpropidine);

morpholine compounds such as (±)-cis-4-[3-(4-tert-butylphenyl)-2-methylpropyl]-2,6-dimethylmorpholine (common name: Fenpropimorph);

organotin compounds such as triphenyltin hydroxide (common name: Fentin hydroxide): triphenyltin acetate (common name: Fentin acetate);

urea compounds such as 1-(4-chlorobenzyl)-1-cyclopentyl-3-phenylurea (common name: Pencycuron);

cinnamic acid compounds such as (E,Z)4-[3-(4-chlorophenyl)-3-(3,4-dimethoxyphenyl)acryloyl] morpholine (common name: Dimethomorph);

phenyl carbamate compounds such as isopropyl 3,4-diethoxycarbanylate (common name: Diethofencarb);

cyanopyrrole compounds such as 3-cyano-4-(2,2-difluoro-1,3-benzodioxol-4-yl)pyrrole (common name: Fludioxonil) and 3-(2',3'-dichlorophenyl)-4-cyanopyrrole (common name: Fenpiclonil);

anthraquinone compounds; crotonic acid compounds; and antibiotics.

When the above-described components, which are usable if necessary, are used in the form of a mixture or in combination with the present hydrazine oxoacetamide derivative or its salt, they are used in such amounts that the weight ratio of the present hydrazine oxoacetamide derivative or its salt to these components is generally in the range of 1:300 to 300:1, desirably 1:100 to 100:1.

EXAMPLES

The following Examples will further illustrate the present invention, which by no means limit the scope of the invention.

Production Example 1

Production of 4-[(4-chlorophenyl)-(ethylaminoxalyl-hydrazono)-methyl]phenyl trifuoromethanesulfonate (Compound 1-5) having the following Formula (XIV):

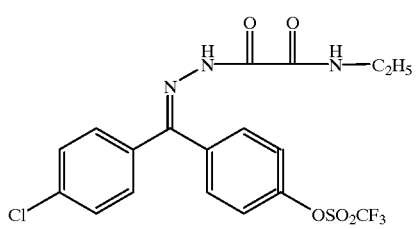

(XIV)

A solution of 0.12 g of sodium methylate in methanol was added to a mixture of 0.93 g of methyl {N'-[(4-chlorophenyl)-(4-trifluoromethanesulfonyloxyphenyl)-methylene]-hydrazino}-oxoacetate, 0.18 g of ethylamine hydrochloride and 8 ml of methanol, and they were stirred at room temperature for 22 hours. Water was added to the obtained reaction liquid, and crystals thus formed were taken by filtration, washed with water and dried to obtain 0.91 g of the title compound.

Production Example 2

Production of 4-[(4-chlorophenyl)-(methylaminoxalyl-hydrazono)-methyl]-phenyl trifluoromethanesulfonate (Compound 1-3) having the following Formula (XV):

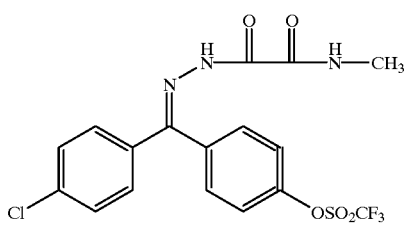

(XV)

A mixture of 4.65 g of methyl {N'-[(4-chlorophenyl)-(4-trifluoromethanesulfonyloxyphenyl)-methylene]-hydrazino}-oxo-acetate (intermediate 5-2), 0.82 g of a 40% solution of methylamine in methanol and 40 ml of methanol was stirred at room temperature for 20 hours. 100 ml of water was poured into the reaction liquid. Crystals thus formed were taken by filtration, washed with water and dried to obtain 4.58 g of the title compound.

Production Example 3

Production of 4-[(4-chlorophenyl)-(ethylaminoxalyl-methyl-hydrazono)-methyl]-phenyl trifluoromethane-sulfonate (Compound 1-180) having the Formula (XVII):

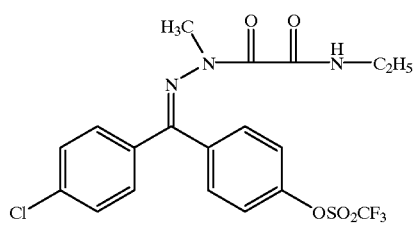

(XVII)

0.46 g of methyl iodide was added to a mixture of 1.44 g of 4-[(4-chlorophenyl)-(ethylaminoxalyl-hydrazono)-methyl]-phenyl trifluoromethanesulfonate, 0.55 g of potassium carbonate and 9 ml of DMF, and the obtained mixture was stirred at room temperature for 20 hours. The reaction liquid was poured into dilute hydrochloric acid. After the extraction with ethyl acetate, an organic layer thus separated was washed with water and then with saturated aqueous salt solution, and dried over magnesium sulfate. Ethyl acetate was evaporated under reduced pressure and the obtained crude product was purified by silica gel column chromatography (eluent: hexane/ethyl acetate=3/1) to obtain 1.10 g of the title compound.

Production Example 4

Production of 4-[(4-chlorophenyl)-(dimethylaminoxalyl-methyl-hydrazono)-methyl]-phenyl trifluoromethane-sulfonate (compound 1-133) of following formula (XVIII):

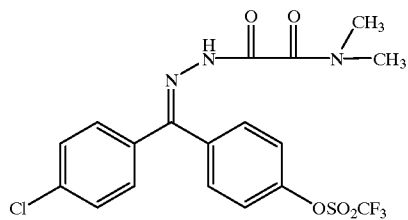

(XVIII)

The reaction was carried out in the same manner as that of Production Example 1 except that ethylamine hydrochloride was replaced with dimethylamine hydrochloride.

Production Example 5

Production of 4-[(4-clorophenyl)-(dimethylaminoxalyl-methyl-hydrazono)-methyl]-phenyl trifluoromethanesulfonate (Compound 1-304) having the following Formula XIX:

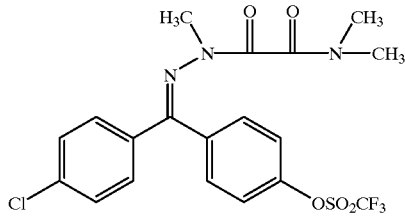

(XIX)

0.22 g of methyl iodide was added to a mixture of 0.6 g of 4-[(4-chlorophenyl)-(dimethylaminoxalyl-hydrazono)-methyl]-phenyl trifluoromethanesulfonate, 0.24 g of potassium carbonate and 5 ml of DMF, and they were stirred at room temperature for 20 hours. The reaction liquid was poured into dilute hydrochloric acid. After the extraction with ethyl acetate, the separated organic layer was washed with water and then with a saturated aqueous salt solution, and dried over magnesium sulfate. Ethyl acetate was evaporated under reduced pressure, and the obtained crude product was purified by silica gel column chromatography (eluent: hexane/ethyl acetate=1/1) to obtain 0.56 g of the title compound.

The physical properties of the compounds obtained in Production Examples 1 to 5 are shown in the following Table 5.

TABLE 5

| Compound No. | m.p. (property) | $^1$H-NMR, (60MHz), (dppm), (TMS) |
|---|---|---|
| 1-3 | 141.0–154.0 (CDCl$_3$) | 2.89(3H, d), 7.10–7.90(9H, m), 10.00, 10.10(1H, s, s) |
| 1-5 | 134.0–139.5 (CDCl$_3$) | 1.20(3H, t), 3.05–3.65(2H, m), 7.10–7.90(9H, m), 10.20(1H, bs) |
| 1-7 | 135.5–138.0 (CDCl$_3$) | 0.95(3H, t), 1.20–2.00(2H, m), 3.00–3.50(2H, m), 6.90–7.90(9H, m), 10.20(1H, bs) |
| 1-27 | 134.5–139.0 (CDCl$_3$) | 3.70–4.05(2H, m), 4.95–5.40(2H, m), 5.45–5.80(1H, m), 7.00–7.80(9H, m), 10.10(1H, bs) |
| 1-37 | 140.5–144.0 (CDCl$_3$) | 2.28(1H, t), 4.18(2H, dd), 7.10–7.80(9H, m), 10.10(1H, s) |
| 1-43 | 150.0–155.0 (CDCl$_3$) | 0.60–1.00(4H, m), 2.50–3.00(1H, m), 6.70–7.90(9H, m), 10.10, 10.20(1H, s, s) |
| 1-133 | glassy (CDCl$_3$) | 3.00(3H, s), 3.47(3H, s), 7.10–7.90(8H, m), 10.10(1H, bs) |
| 1-178 | glassy (CDCl$_3$) | 2.5–3.85(6H, m), 6.80–7.90(9H, m) |
| 1-180 | glassy (CDCl$_3$) | 1.13(3H, t), 2.93, 3.64(3H, s, s), 3.27 (2H, m), 6.60–7.90(9H, m) |
| 1-182 | glassy (CDCl$_3$) | 0.92(3H, t), 1.20–1.90(2H, m), 2.70–3.80(5H, m), 6.60–7.90(9H, m) |
| 1-202 | glassy (CDCl$_3$) | 2.92, 3.64(3H, s, s), 3.60–4.05(2H, m), 4.85–5.40(2H, m), 5.45–6.20(1H, m), 6.60–7.90(9H, m) |
| 1-218 | glassy (CDCl$_3$) | 0.30–1.00(4H, m), 2.50–3.70(4H, m), 6.60–7.90(9H, m) |
| 1-304 | glassy (CDCl$_3$) | 2.60–3.40(9H, m), 7.00–7.70(8H, m) |
| 1-515 | 157.0–159.2 (CDCl$_3$) | 2.90(3H, d), 7.07–7.80(9H, m), 10.10, 10.19(1H, s, s) |
| 1-517 | 135.6–139.6 (CDCl$_3$) | 1.20(3H, t), 3.12–3.58(2H, m), 7.08–7.80(9H, m), 10.20(1H, bs) |
| 1-555 | 179.7–184.4 (CDCl$_3$) | 0.75(4H, d), 2.58–2.97(1H, m), 7.10–7.82 (9H, m), 10.10, 10.21(1H, s, s) |
| 2-6 | 135.5–146.1 (CDCl$_3$) | 1.20(3H, t), 3.12⊥3.57 (2H, m), 4.12, 4.20(2H, s,s), 7.24⊥7.65 (9H, m), 10.15(1H, s) |

Preparation Examples wherein the present hydrazine oxoacetamide derivative or its salt is used in a insecticide will be given below. In Preparation Examples, parts are given by weight.

Preparation Example 1 (Wettable Powder)

50 parts of each compound finely pulverized to a particle diameter of 10 μm, 3 parts of sodium lignin sulfonate, 2 parts of sodium laurylsulfate, 10 parts of synthetic hydrous silicic acid and 35 parts of clay were thoroughly mixed together. The obtained mixture was pulverized with a jet mill to obtain a wettable powder.

Preparation Example 2 (Emulsion)

10 parts of each compound, 9 parts of polyoxyethylene styrenated phenyl ether, 6 parts of calcium dodecylbenzenesulfonate and 75 parts of xylene were homogeneously mixed together to obtain an emulsion.

Preparation Example 3 (Aqueous Suspension)

25 parts of Compound A-2 or 14 finely pulverized to a particle diameter of 5 μm with a hammer mill, 3 parts of ammonium polyoxyethylene styrenated phenyl ether sulfate, 62 parts of water and a small amount of an antifoaming agent were mixed together. The obtained mixture was wet-ground to an average particle size of 2 μm, and then mixed with 10 parts of a solution previously prepared from 2 parts of xantham gum, 1 part of an antiseptic, 50 parts of ethylene glycol and 47 parts of water to obtain a suspension.

Preparation Example 4 (Wettable Granules)

40 parts of each compound finely pulverized to a particle diameter of 5 μm with a hammer mill, 23 parts of fine clay powder, 20 parts of ammonium sulfate powder, 5 parts of sodium lignin sulfonate and 1 part of sodium laurylsulfate were mixed together. The obtained mixture was further pulverized with a jet mill. 15 parts of water was added to the mixture. After further mixing, the obtained mixture was extruded through a 0.8 mm screen to obtain particles, which were dried at 70. After cutting the obtained product to a length of about 1 to 1.5 mm, they were filtered to obtain wettable granules.

Biological Test Example 1

Effect on *Spodoptera litura*:

An emulsion was prepared from each of the present compounds listed below, in the same manner as that of Preparation Example 2. The obtained emulsion was diluted with water so that the concentration of the present compound would be 50 ppm, 5 ppm or 0.5 ppm to obtain diluted aqueous emulsions.

The diluted aqueous emulsions were sprayed on leaves of Chinese cabbages of a 3–4 leave stage. After drying with air, the leaves were placed in a plastic vessel having a size of 21 cm×13 cm×3 cm (depth). Ten third-instar larvae of Spodoptera litura were released in the vessel. The vessel was closed and placed in a room kept at a constant temperature of 26. 48 hours after, the numbers of surviving and dead ones were counted, and the death rate was calculated.

The results are shown in Table 6 below, together with those obtained with the comparative compounds.

TABLE 6

(Effect on *Spodoptera litura*)

| Compound No. | Concentration (ppm) | | |
|---|---|---|---|
| | 50 | 5 | 0.5 |
| 1-3 | 100 | 100 | 50 |
| 1-5 | 100 | 100 | 100 |
| 1-7 | 100 | 100 | 70 |
| 1-27 | 100 | 100 | 70 |
| 1-37 | 100 | 100 | 60 |
| 1-43 | 100 | 100 | 90 |
| 1-133 | 100 | 100 | 90 |
| 1-178 | 100 | 100 | 30 |
| 1-515 | 100 | 100 | 75 |
| 1-517 | 100 | 100 | 60 |
| 1-555 | 100 | 100 | 40 |
| 2-6 | 100 | 100 | 50 |
| A | 100 | 90 | 0 |
| B | 100 | 100 | 0 |
| C | 100 | 0 | — |
| D | 0 | 0 | — |
| E | 0 | — | — |
| F | 0 | — | — |
| G | 10 | — | — |

Notes) Comparative compounds A to G in Table 6 were as follows:

Comparative compound A: Compound of Formula (II)
Comparative compound B: Compound of Formula (III)
Comparative compound C: Compound of Formula (V)
Comparative compound D: Intermediate product 5-4
Comparative compound E: Compound of Formula (VI)
Comparative compound F: Intermediate product 5-53
Comparative compound G: Intermediate product 5-79

Biological Test Example 2

Effect on *Plutella xylostella*

Emulsions of varied concentrations prepared in the same manner as that of the above Biological Test Example 1 were sprayed on leaves of Chinese cabbages of a 3–4 leave stage. After drying with air, the leaves were placed in a plastic vessel having a size of 9 cm (inside diameter)×6.5 cm (depth). Ten third-instar larvae of *Plutella xylostella* were released in the vessel. The vessel was closed and placed in a room kept at a constant temperature of 26. 48 hours after, the numbers of surviving and dead ones were counted, and the death rate was calculated. The results are shown in following Table 7 together with those obtained with comparative compounds.

TABLE 7

Effect on *Plutella xylostella*

| Compound No. | Concentration (ppm) | | |
|---|---|---|---|
| | 50 | 5 | 0.5 |
| 1-3 | 100 | 100 | 0 |
| 1-5 | 100 | 100 | 0 |
| A | 100 | 20 | 0 |
| B | 100 | 0 | 0 |

Biological Test Example 3

Effect on *Mamestra brassicae*:

The insecticidal activities of the compounds of concentrations shown in Table 8 below were evaluated in the same manner as that of Biological Test Example 1.

TABLE 8

| Compound No. | Concentration (ppm) | | |
|---|---|---|---|
| | 50 | 2.5 | 1.25 |
| 1-3 | 100 | 89 | 67 |
| 1-5 | 100 | 100 | 89 |
| 1-7 | 100 | 70 | 50 |
| 1-27 | 100 | 100 | 80 |
| 1-37 | 100 | 100 | 70 |
| 1-43 | 100 | 67 | 33 |
| 1-133 | 100 | 100 | 44 |
| 1-515 | 100 | 80 | 60 |
| 1-517 | 100 | 100 | 100 |
| A | 0 | 0 | 0 |
| B | 33 | 0 | 0 |

Biological Test Example 4

Effect on *Spodptera exigua*:

An emulsion was prepared from each of the present compounds listed below, in the same manner as that of Preparation Example 2. The obtained emulsion was diluted with water so that the concentration of the present compound would be a predetermined one. The diluted aqueous emulsions were sprayed on leaves of cucumbers of a 2–3 leave stage. After drying with air, the leaves were placed in a plastic vessel having a size of 9 cm (inside diameter)×6.5 cm (depth). Ten third-instar larvae of *Spodptera exigua* were released in the vessel. The vessel was closed and placed in a room kept at a constant temperature of 26. 48 hours after, the numbers of surviving and dead ones were counted, and the death rate was calculated. The results are shown in Table 9 below together with those obtained with comparative compounds.

TABLE 9

(Effect on *Spodptera exigua*)

| Compound No. | Concentration (ppm) | | | | |
|---|---|---|---|---|---|
| | 5 | 2.5 | 1.25 | 0.63 | 0.32 |

Biological Test Example 5

Effect on Adoxophyes sp.:

The insecticidal activities of the compounds having the concentrations shown in Table 10 below were examined in the same manner as that of Biological Test Example 4.

TABLE 10

(Effect on *Adoxophyes sp.*)

| Compound No. | Concentration (ppm) | | | | |
|---|---|---|---|---|---|
| | 5 | 2.5 | 1.25 | 0.63 | 0.32 |

Biological Test Example 6

Peroral acute toxicity for mouse:

Each of the present compounds was suspended in a 0.5% aqueous carboxymethylcellulose solution to obtain a suspension of a predetermined concentration. Male SIc:ICR mice (SPF) of 6 weeks old (body weight: 29.5 to 34.4 g) were fasted for 3 hours. 1 ml, per 100 g of the body weight, of the suspension was forcibly fed into the stomach of each mouse. Then, a food and water were given to the mice and they were bred in a cage. The observation period after the administration was 7 days. During that period, the life and death, general conditions and change in body weight of the mice were observed. Thereafter, pathologico-anatomic experiments were carried out (two mice in each group).

When 300 mg/kg of Compound No. 1-5 was used, the results were as follows: Neither death nor abnormality of the general conditions was recognized, the body weight of the rat increased normally, and no abnormality was found in the dissection view after the completion of the observation.

It is thus understood that the compounds of the present invention have an insecticidal activity superior to that of publicly known hydrazine oxoacetamide-related compounds particularly at a low concentration and that these compounds have a high safety on animals.

The present application is a continuation of PCT application JP 99-05760 filed Oct. 19, 1999, upon which priority is requested based on 35 USC 120, based on Japanese application Serial Number 10-297240 filed Oct. 19, 1998 upon which priority is requested based on 35 USC 119.

Obviously, numerous modifications and variations of the present invention are possible in light of the above teachings. It is therefore to be understood that within the scope of the appended claims, the invention may be practiced otherwise than as specifically described herein

What is claimed is:

1. A hydrazine oxoacetamide derivative having the following formula or a salt thereof:

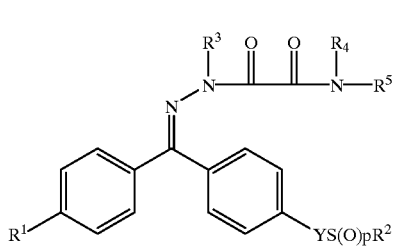

wherein $R^1$ represents a chlorine atom or a bromine atom,

Y represents an oxygen atom or a methylene group, and when Y is an oxygen atom, p is 2 and when Y is a methylene group, p is 0, $R^2$ represents a trifluoromethyl group, $R^3$ represents a hydrogen atom or a methyl group, $R^4$ represents a hydrogen atom or a methyl group, and $R^5$ represents a methyl group, an ethyl group, an n-propyl group, a cyclopropyl group, an allyl group or a propargyl group.

2. The hydrazine oxoacetamide derivative or its salt of claim 1 wherein $R^1$ represents a chlorine atom.

3. The hydrazine oxoacetamide derivative or its salt of claim 1 wherein $R^5$ represents an ethyl group.

4. An insecticide containing the hydrazine oxoacetamide derivative or its salt of claim 1 as an active ingredient.

5. The insecticide of claim 4, which is effective against *Spodoptera litura, Plutella xylostella, Mamestra brassicae, Spodptera exigua* or Adoxophyes sp.

6. The insecticide of claim 4, which contains 0.002 to 80% by weight of the hydrazine oxoacetamide derivative or its salt.

7. The insecticide of claim 4, which contains 0.01 to 70% by weight of the hydrazine oxoacetamide derivative or its salt.

8. A process for producing a hydrazine oxoacetamide derivative of claim 1, which comprises reacting a compound having the following Formula (VIII):

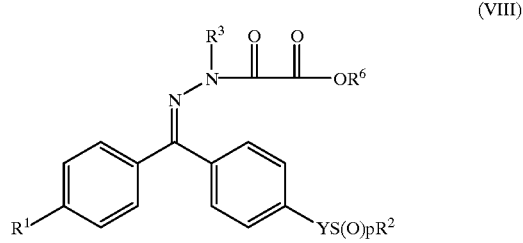

wherein $R^1$ represents a chlorine atom or a bromine atom, $R^2$ represents a trifluoromethyl group, $R^3$ represents a hydrogen atom or a methyl group, and Y represents an oxygen atom or a methylene group, and when Y is an oxygen atom, p is 2 and when Y is a methylene group, p is 0, with a compound having the following Formula (IX):

wherein $R^4$ represents a hydrogen atom or a methyl group, and $R^5$ represents a methyl group, an ethyl group, an n-propyl group, a cyclopropyl group, an allyl group or a propargyl group.

9. A process for producing a hydrazine oxoacetamide derivative of claim 1, which comprises reacting a compound having the following Formula (X):

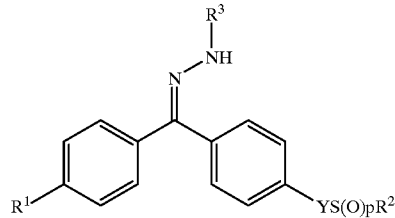

wherein $R^1$ represents a chlorine atom or a bromine atom, $R^2$ represents a trifluoromethyl group, $R^3$ represents a hydrogen atom or a methyl group, and Y represents an oxygen atom or a methylene group, and when Y is an oxygen atom, p is 2 and when Y is a methylene group, p is 0, with a compound having the following Formula (XI):

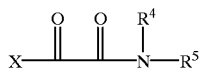

(XI)

wherein
- $R^4$ represents a hydrogen atom or a methyl group,
- $R^5$ represents a methyl group, an ethyl group, an n-propyl group, a cyclopropyl group, an allyl group or a propargyl group, and
- X represents a halogen atom.

10. A process for producing a hydrazine oxoacetamide derivative of claim 1, which comprises reacting a compound having the following Formula (1):

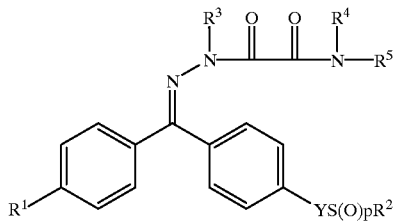

(I)

wherein
- $R^1$ represents a chlorine atom or a bromine atom,
- Y represents an oxygen atom or a methylene group, and when Y is an oxygen atom, p is 2 and when Y is a methylene group, p is 0,
- $R^2$ represents a trifluoromethyl group,
- $R^3$ and $R^4$ each represent a hydrogen atom or a methyl group, with the proviso that one or both of $R_3$ and $R_4$ are hydrogen atoms, and
- $R^5$ represents a methyl group, a ethyl group, an n-propyl group, a cyclopropyl group, an allyl group or a propargyl group;

with a compound having the following Formula (XII):

X—R⁷  (XII)

wherein $R^7$ represents a methyl group, or with a compound having the following Formula (XIII):

$(R^8O)_2SO_2$  (XIII)

wherein $R^8$ represents a methyl group.

* * * * *

UNITED STATES PATENT AND TRADEMARK OFFICE
CERTIFICATE OF CORRECTION

PATENT NO. : 6,399,659 B2
DATED : June 4, 2002
INVENTOR(S) : Usui et al.

It is certified that error appears in the above-identified patent and that said Letters Patent is hereby corrected as shown below:

<u>Title page,</u>
Item [63], the Related U.S. Application Data, should read:

-- Related U.S. Application Data
[63]    Continuation of application No. PCT/JP99/05760, filed on Oct. 19, 1999. --

<u>Column 1,</u>
Lines 4 and 5, should read:
-- This application is a continuation of PCT/JP99/05760 filed Oct. 19, 1999. --

Signed and Sealed this

Twentieth Day of May, 2003

JAMES E. ROGAN
*Director of the United States Patent and Trademark Office*